United States Patent [19]
Andresen

[11] Patent Number: 6,126,804
[45] Date of Patent: *Oct. 3, 2000

[54] INTEGRATED POLYMERASE CHAIN REACTION/ELECTROPHORESIS INSTRUMENT

[75] Inventor: Brian D. Andresen, Livermore, Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/935,936

[22] Filed: Sep. 23, 1997

[51] Int. Cl.[7] .......................... G01N 27/26; G01N 27/447
[52] U.S. Cl. .......................... 204/601; 204/450; 204/451; 204/452; 204/600; 204/603; 435/287.2; 435/288.5
[58] Field of Search ..................... 204/601, 602, 204/603, 604, 605, 451, 452, 453, 454, 455, 450, 600; 435/287.2, 287.1, 287.3, 288.5

[56] References Cited

U.S. PATENT DOCUMENTS

| | | | |
|---|---|---|---|
| 5,235,409 | 8/1993 | Burgi et al. | 204/452 X |
| 5,436,129 | 7/1995 | Stapleton | 204/450 X |
| 5,439,578 | 8/1995 | Dovichi et al. | 204/603 |
| 5,661,028 | 8/1997 | Foote | 435/287.2 |
| 5,716,825 | 2/1998 | Hancock et al. | 435/286.5 |
| 5,824,204 | 10/1998 | Jerman | 204/601 |
| 5,856,174 | 1/1999 | Lipshutz et al. | 435/287.2 X |

OTHER PUBLICATIONS

A.T. Woolley et al "Functional Integration of PCR Amplification and Capillary Electrophoresis in a Microfabricated DNA Analysis Device" Analytical Chemistry, vol. 68, No. 23 (Dec. 1, 1996) 4081–4086.

A.T. Woolley et al "Ultra–high–speed DNA fragment separations using microfabricated capillary array electrophoresis chip" Proceedings of the National Academy of Science, USA vol. 91 (Nov. 1994) 11348–11352.

M.A. Burns "Microfabricated structures for integrated DNA analysis" Proceedings of the National Academy of Science, USA vol. 93 (May 1996) 5556–596.

*Primary Examiner*—Jill Warden
*Assistant Examiner*—John S. Starsiak, Jr.
*Attorney, Agent, or Firm*—L. E. Carnahan; Alan H. Thompson

[57] ABSTRACT

A new approach and instrument for field identification of micro-organisms and DNA fragments using a small and disposable device containing integrated polymerase chain reaction (PCR) enzymatic reaction wells, attached capillary electrophoresis (CE) channels, detectors, and read-out all on/in a small hand-held package. The analysis instrument may be made inexpensively, for example, of plastic, and thus is disposable, which minimizes cross contamination and the potential for false positive identification between samples. In addition, it is designed for multiple users with individual applications. The integrated PCR/CE is manufactured by the PCR well and CE channels are "stamped" into plastic depressions where conductive coatings are made in the wells and ends of the CE microchannels to carry voltage and current to heat the PCR reaction mixtures and simultaneously draw DNA bands up the CE channels. Light is transmitted through the instrument at appropriate points and detects PCR bands and identifies DNA fragments by size (retention time) and quantifies each by the amount of light generated as each phototransistor positioned below each CE channel detects a passing band. The instrument is so compact that at least 100 PCR/CE reactions/analyses can be performed easily on one detection device.

18 Claims, 4 Drawing Sheets

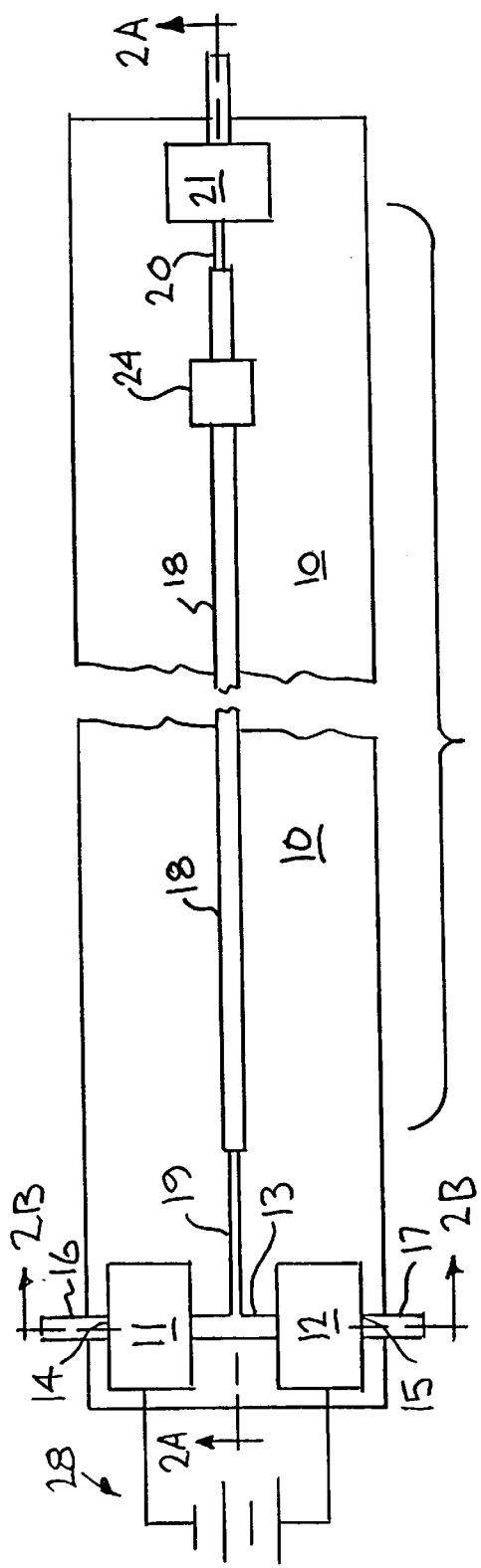
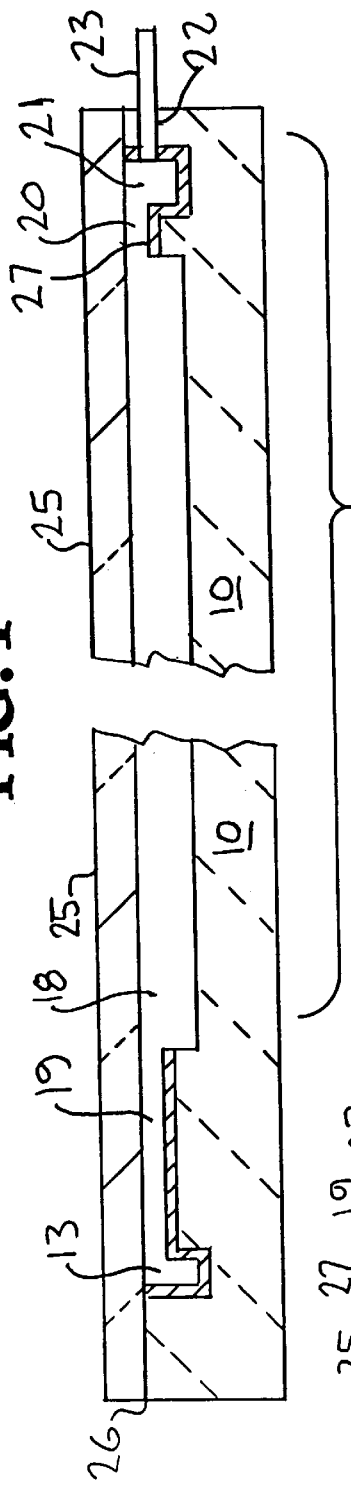
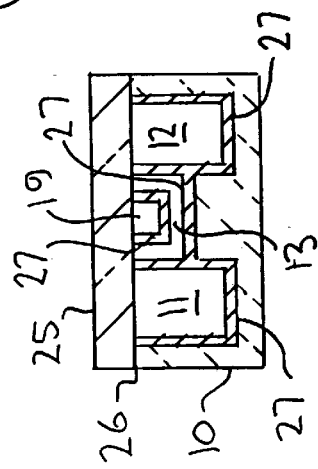
FIG. 1
FIG. 2A
FIG. 2B

INTEGRATED POLYMERASE CHAIN REACTION/ELECTROPHORESIS INSTRUMENT

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to detection of micro-organisms, particularly to the identification organisms by fingerprinting biochemicals and DNA fragments, and more particularly to an inexpansive, small multiple channel PCR/CE instrumentation for rapidly identifying micro-organisms and DNA fragments.

The detection of micro-organisms in the field will be an essential element of any future military action. The identification of threat organisms by fingerprinting biochemicals and DNA fragments has matured to a point that in the laboratory specific identifications can be made. However, the laboratory instrumentation is not readily adapted for field applications.

The analysis of DNA fragments by electrophoresis is well established and essential for all types of genetic and biochemical studies. A thin electrophoresis gel is prepared, poured, and a potential of 100–300 volts (20–100 milliamps) applied. Separation of DNA fragments can take from 1–8 hours, depending upon the resolution desired and hardness of the gel. Preparing the gels, adding samples to each electrophoresis lane, separating, staining, and identifying DNA fragments visually is time consuming.

Standard DNA analysis methods sometime require hundreds of samples to be analyzed simultaneously. After electrophoretic separation, the gel must be stained and photographed in order to generate a permanent record which requires manipulation of the gel material and potential exposure to toxic staining chemicals. The electrophoric gels are prepared either from agarose or polyacrylamide and they are typically used only once. These water based gels will not store well without drying out and deteriorating within a few hours. Thus, these gels are not suitable for field use.

Although gel electrophoresis has been the cornerstone of genetic research, the current analytical technique is labor intensive, slow, and difficult to perform in a fully automated manner. What is needed is a multisample analysis device which can: 1) rapidly screen samples, 2) requires minimum sample preparation, 3) has sensitive and precise separation capabilities, 4) is attractive to researchers already performing standard gel electrophoresis, and 5) can be easily and quickly used in the field.

Capillary electrophoresis (CE) is one approach which has become increasingly more popular in the last few years, and more commercial CE systems are now available. CE is fast, accurate, highly specific, and requires only minimum (mL) amounts of sample. Small, 50–100 micron internal diameter (i.d.) and 10–20 cm long, capillary tubes perform exceptionally well and typically have 100,000–800,000 theoretical-plate separation characteristics. Because of the small capillary size, the heat dissipation of the column is very good and thermal peak broadening is almost nonexistent. Although, performing high resolution separations of DNA bands within minutes, commercial CE instruments are configured only with a single column.

In addition to analyzing only one sample at a time, an interface between polymerase chain reaction (PCR) sample preparation and commercial capillary electrophoresis instruments does not exist. PCR samples must be manually transferred to the CE instrument for analysis. This is very time consuming and difficult when only a limited amount of sample is available. Although CE is faster than gel electrophoresis, a CE system which analyzes many samples in parallel does not exist and no methods are now available to directly and immediately analyze the products of the PCR reactions.

The present invention provides a solution to the above-mentioned drawbacks of the existing analysis systems and provides multiple channel integrated PCR/CE instrumentation to rapidly identify micro-organisms and DNA fragments. The instrumentation provided by this invention enables field use and is of a "throw-away" nature, thus minimizing cross contamination and the potential for false positive identification between samples, as well as being designed for multiple users with individual applications. The integral PCR/CE instrument can be manufactured from plastic and eliminates the complicated electronic hardware of previous instruments, while being compact (hand-held). The instrument is small and compact so that 100 PCR/CE reactions/analyses can be performed easily on one detection device.

SUMMARY OF THE INVENTION

It is an object of the present invention to provide integrated PCR/CE instrumentation.

A further object of the invention is to provide a multiple channel, hand held PCR/CE instrument.

A further object of the invention is to provide a small, inexpensive instrument for rapid identification of micro-organisms and DNA fragments in a field environment.

Another object of the invention is to provide a multi-channel integrated PCR/CE instrument which is inexpensively constructed and is disposable.

Another object of the invention is to provide a multi-channel integrated PCR/CE instrument for rapid identification of micro-organisms and DNA fragments which is small, disposable, and has field use capability.

Another object of the invention is to provide an integrated PCR/CE instrument which can be constructed of plastic and utilizes a conductive coating which functions for heating of the PCR reaction mixtures and simultaneously drawing DNA bands through the CE channels, and includes a detection arrangement to identify material passing through each CE channel.

Other objects and advantages will become apparent from the following description and accompanying drawings. The invention is an integrated PCR/CE instrument for rapidly identifying micro-organisms and DNA fragments under field operation conditions. This new approach to detection and identification of micro-organisms involves an instrument for the field that is a small and disposable device containing integrated PCR enzymatic reaction wells, attached capillary gel electrophoresis channels, detectors, and readout, all on/in a small hand-held package. This new analysis device, made of plastic, has the potential to supercede any current analysis methods for DNA characterization both in the laboratory and in the field. Also, the "throw-away" nature of the instrument minimizes cross contamination and potential for false positive identification between samples. For mass production, the instrument does not need to utilize microchip technology to incorporate electrical components, can be produced rapidly and very inexpensively, and is designed for multiple users with individual applications. Because the new instrument does not rely on micro-chip technology, no complicated electronic hardware is needed, yet the design is very small and compact. The instrument may be fabricated from plastic (or silica) with multiple, up to 100, capillary lanes and depressions for CE buffers and PCR reaction solutions. The integrated PCR/CE may be manufactured such that the PCR/CE wells and CE channels are "stamped" into plastic depressions where conductive coatings are made in the wells and ends or micro-channels of the CE channels to carry voltage and current to heat the PCR reaction mixtures and simultaneously drawn DNA bands up the CE channels. Light is transmitted through the instrument at the appropriate point on the CE channels that detects PCR bands and identifies DNA fragments by size (retention time) and quantifies each by the amount of light generated as each phototransistor (positioned below each CE channel) detects a passing band. The design of the instrument is so compact that up to 100 and higher PCR/CE reactions/analyses can be performed easily on a detection device.

The invention will find use in applications such as detection of biological warfare organisms, water purity measurements and pathogen identification in the field, identification of unknown illness, charcterization of DNA and identification of biological samples, and analysis of DNA fragments and biological experiments in gene and DNA/RNA manipulation.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1 is a view of a single channel integrated PCR/CE instrument without a top cover made in accordance with the present invention.

FIG. 2A is an enlarged; Shortened, cross-sectional side view of the FIG. 1 instrument, taken along line 2A—2A of FIG. 1, but with a top cover.

FIG. 2B is a cross sectional view taken along line 2B—2B of FIG. 1.

DETAILED DESCRIPTION OF THE INVENTION

The invention involves a new approach and instrumentation in the field of identification of-organisms by fingerprinting biochemicals and DNA fragments. The invention provides an instrument for field use, the instrument being small and disposable. The instrument contains integrated PCR enzymatic reaction wells, attached capillary gel electrophoresis channels, detectors, and read-out all in/on a small hand-held package. The instrument is so compact the it enables performance of up to 100 PCR/CE reactions/analyses on one detection device. An instrument may be made of plastic, for example, wherein the PCR wells and CE channels are "stamped" in the plastic to form depressions and capillary lanes whereafter conductive coatings are applied in the depressions or PCR/CE buffer wells and ends of the CE micro-channels to carry voltage and current to heat the PCR reaction mixtures and simultaneously draw DNA bands along the CE channels. Light is transmitted through the instrument at an appropriate point along each channel which detects PCR bands and identifies DNA fragments by size (retention time) and quantifies each by the amount of light generated as each phototransistor (positioned below each CE channel) detects a passing band.

A 100 channel integrated PCR/CE system can simultaneously analyze the reaction products of 100 PCR reactions. In addition, the system of this invention is ideal where the PCR reaction products are loaded directly into each capillary lane immediately following the PCR heat-cycle sequences. This eliminates the prior separate handling, reduces the costs, and greatly decreases the analysis time.

Figure 3:
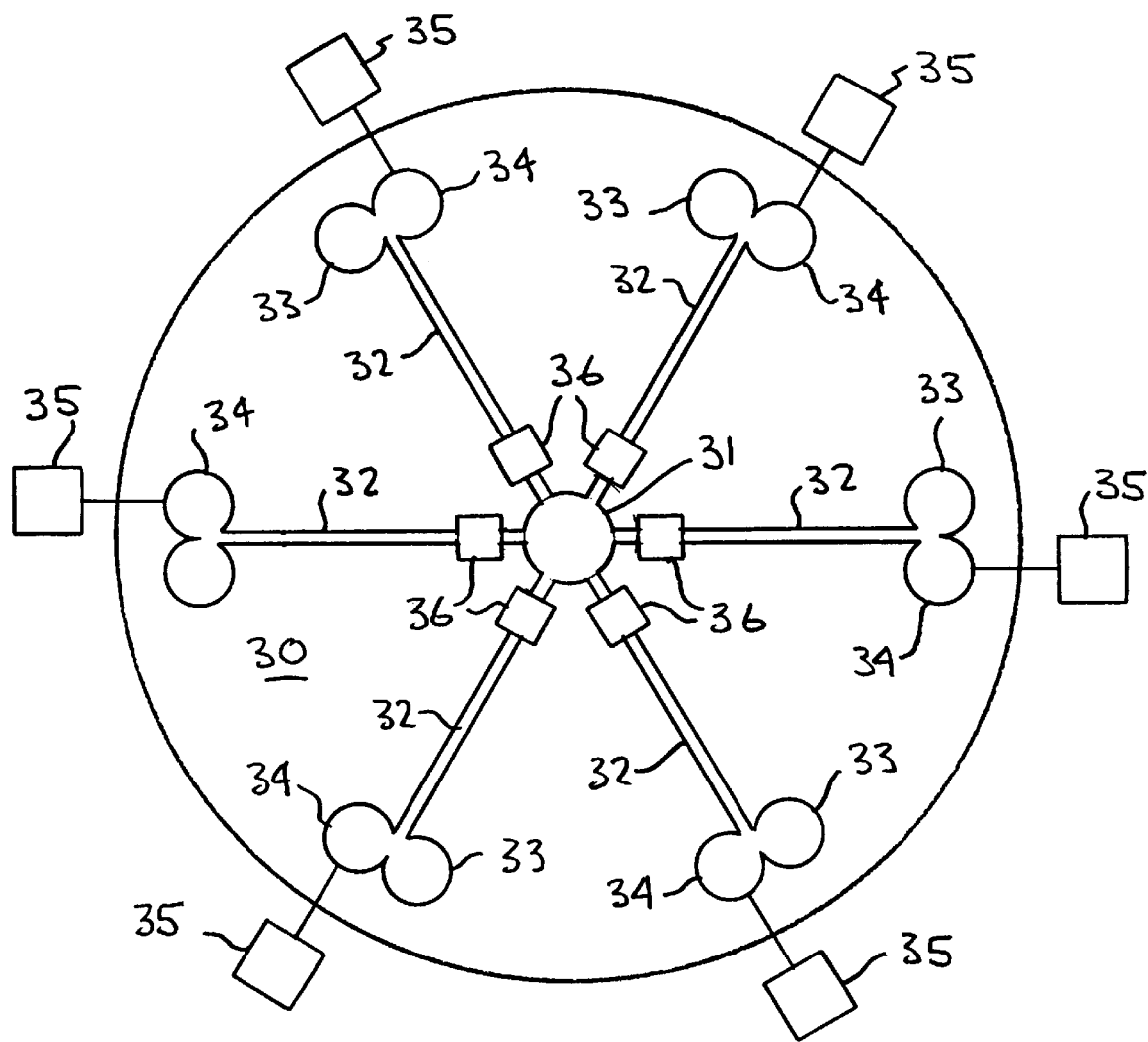
FIG. 3 schematically illustrates an embodiment utilizing multiple PCR/CE channels.

A plastic sheet is embossed, or silica wafer etched, for example, and designed and fabricated with, for example, up to 100 capillary lanes or channels with combined depressions or wells for CE buffers and PCR reaction solutions. The lanes only need to be a few inches long and a few tenths of millimeters wide and deep. For example, the length of the lanes or channels may be 1" to 3", with a width of 50 to 100 microns, and depth of 10 to 100 microns, with a separation distance between lanes being about 1–10 nm. Thus, a 100 lane instrument, with CE buffers and PCP wells, can be formed on a rectangular wafer or member having a width of 3" and length of 3", or on a circular wafer having a diameter of 3". The thus formed channels and wells are covered by a glass or clear plastic member, or other nonconductive material. As shown in FIG. 1, at least one CE buffer well is located at each end of a channel or lane and a PCR well is located at one end of each channel or lane, wherein the PCR chemicals and CE buffers are added. This may be accomplished by supply or feed lines extending into small ports or opening adjacent each well. Electrical conductors are integrated into both CE buffer and PCR wells so that an electrical potential can be applied to each of the capillaries. This can be accomplished by coating the wells and ends of the channels with a conductive coating, such as chemically reduced Pt/Pd, Ag, Sn, etc. applied using, for example, a polyolidine co-polymer base As pointed out above, the instrument can be rectangular or circular, and if a circular wheel design is used, it would contain only one central buffer depression or well at each of the inner ends of the channels or lanes and a single electrical contact for all the CE lanes or channels, as illustrated in FIG. 3; with both CE buffer and PCR wells located at the outer ends of each channel or lane. This multi-channel PCR/CE instrument may be manufactured so inexpensively so that it is disposable, eliminating any possibility of cross contamination.

A depression formed in the substrate of only a few microns deep (10 to 100) and a diameter of 2 to 10 mm at one end of each CE lane or channel can serve as the PCR synthesis area or reaction chamber. Initially this well would be filled with PCR primers, enzyme and nucleotides and overlaid with a dear glass or plastic cover or mineral oil to decrease sample evaporation during the heating cycle. The well can be filled with the selected PCR solution or chemical materials via openings, as shown in FIG. 1. The appropriate heating sequence is then applied to the PCR solution with an external sandwich heater. Following appropriate PCR cycling, the connection is made to the other end of the capillary lane for electrophoretic separations of the synthetic products, as conventionally carried out in capillary electrophoresis devices. All reactions are performed on micronliters ($\mu$l) amounts of material and no PCR reaction products will be manually transferred to each capillary lane. In order to apply small amounts of sample to the CE channel or lane, an electrical bias is applied between the PCR reaction chamber or well and the adjacent buffer solution well, as indicated in FIG. 1. This has the advantage of keeping excess PCR products and reagents from feeding into the CE lane during DNA fragment separations.

As the synthesized DNA fragments migrate along the capillary lanes or channels, a detector is positioned to measure both the number of bands and how long it takes each band to travel completely along the capillary channel under a fixed or varying potential. Many methods are available to detect DNA in gels. However, DNA detection with a capillary system requires either some type of electrochemical redox detector, index-of-refraction, or calorimetric measurement with an optical detector.

Figure 5:
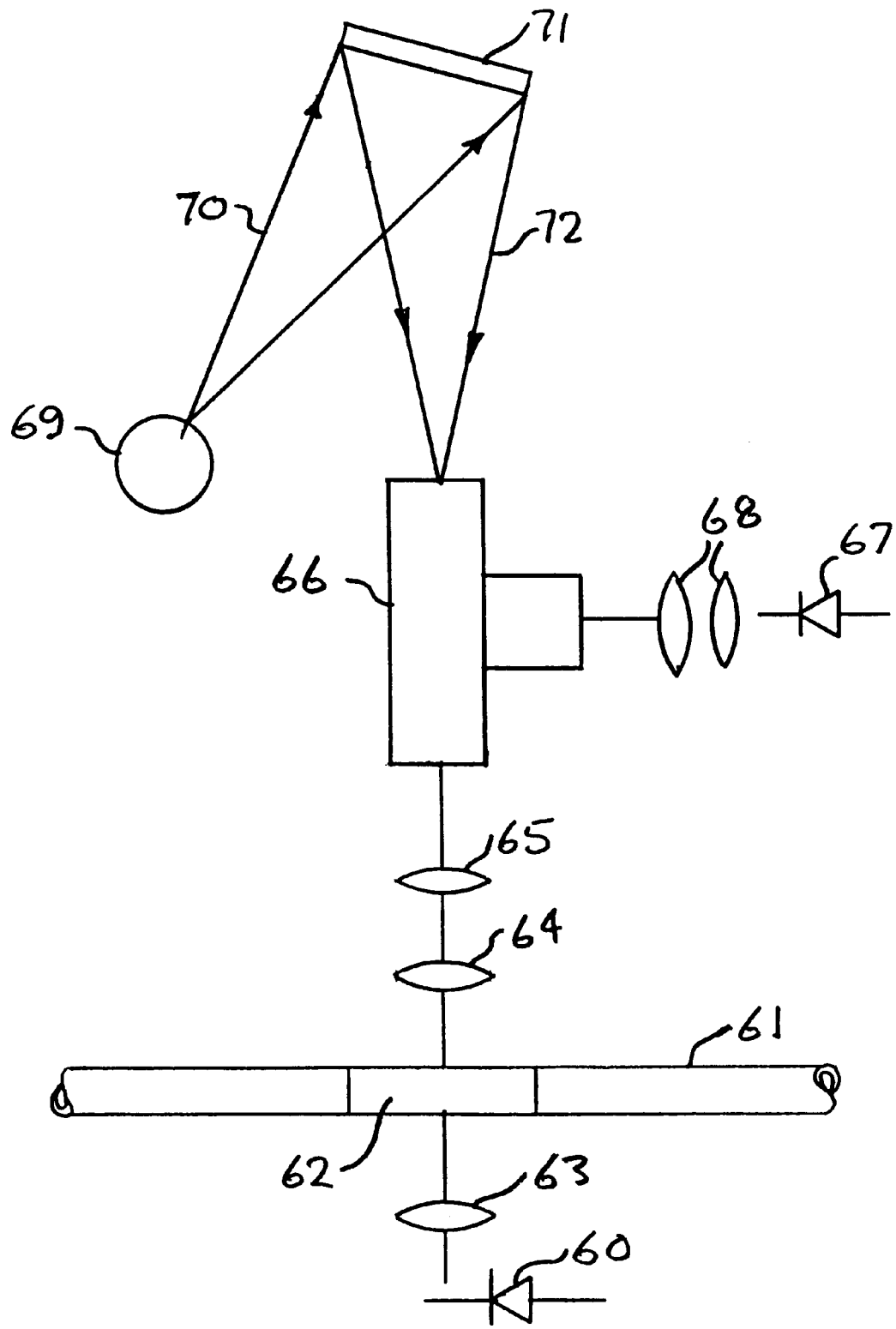
FIG. 5 schematically illustrates a currently available (prior art) detection arrangement that can be utilized with the integrated PCR/CE arrangement of this invention.

The detection of nano-molar amounts of DNA, particularly for a multi-channel integrated PCR/CE system, has not been previously accomplished. The sensitivity of the detection can be increased if each DNA band is initially tagged with a highly fluorescent label. Ideally, a photodiode and lens positioned above each capillary lane can be utilized to sense the passing of a fluorescent DNA fragment through an illuminated gap. Such a detection system is illustrated in FIG. 5.

An array of 100 photodiodes needs to be incorporated into a 100 channel PCR/CE system. This can be accomplished if the disposable PCR/CE wafer is first laid on top of a permanent photodiode array assembly Ace containing PCR heaters, electrical connectors, and general purpose ultraviolet (UV) lamp. Finally, all the 100 signals from the channels are multiplexed every few milliseconds, computer processed, stored and displayed as a time vs. signal amplitude. The time it takes the standard DNA "ladder" fragments to migrate along the CE lane or channel will be compared to the unknowns applied to one or more of the adjacent CE channels.

Referring now to the drawings, FIGS. 1 and 2A–2B illustrate an embodiment of a single lane or channel integrated PCR/CE instrument. This prototype instrument comprises a rectangular substrate 10 formed, for example, of plastic or silica, at one end of which contains a PCR well or reaction chamber 11 and a CE buffer well 12 which are interconnected by a passageway 13. If desired the wells 11 and 12 may be connected by openings 14 and 15 for connection to supply tubes 16 and 17. A capillary column, lane or channel 18 having reduced sections 19 and 20 at each end extends along the substrate 10 with reduced section 19 intersecting passageway 13 and reduced section 20 terminating in a CE buffer well 21. Buffer well 21 may be provided with an opening 22 for connection to a supply tube 23. A photodetector 24, such as a photodiode, is positioned adjacent CE channel or land 18. As seen in FIG. 2, a glass or transparent non-conductive cover plate 25 is positioned over the substrate 10 and bonded thereto as indicated at 26. The wells 11, 12, and 21 along with passageway 13 and channel sections 19 and 20 are provided with a coating 27 of a thin electrically conductive material such as Pt/Pd, Ag, or Sn, which is connected to a power supply 28. The supply opening in the wells 11, 12 and 21 may be omitted and the wells filled or loaded prior to attaching the cover plate 25 with the desired reagents and buffers, or the wells can be filled through the openings and the openings filled with mineral oil to keep evaporation of the aqueous media to a minimum. The wells 11, 12, and 21 only need to hold a volume of 10–20 $\mu$l of solution. The total size of the buffer wells 12 and 21 and the PCR well 11 is 200–400 microns across, and the capillary column is about 100 microns wide and 10 microns deep, with the reduced sections 19 and 20 having a width of 2 mm, depth of 1 mm, and lengths of 1" and 2", respectively.

In operation, the buffer-wells and column or lane are first filled with a buffer solution. The PCR well is charged and then the whole system is allowed to cycle through the heat/cool PCR sequence. Voltage switching allows the PCR products to reside for a moment at the "T", formed by the interconnection passageway and the channel or lane, where a small fraction of the synthetic DNA is drawn by high voltage potential into the capillary channel. The PCR solution is then forced back into the well so that clean buffer material allows only a pure aliquot to be introduced into the column or channel. The entire process is easily controlled with a small microprocessor.

FIG. 3 schematically illustrates an embodiment of a multi-channel circular wheel integrated PCR-CE instrument wherein six (6) columns or channels feed into a central buffer well. As shown, the circular substrate 30 is provided with a central buffer well 31, a plurality, six in this embodiment, capillary columns, channel or lanes 32 extending radially outward from central buffer well 31, a PCR well 33 and an outer buffer well 34 connected to each of capillary columns 32, each having an electrical power supply 35 connected thereto, and a photodetector 36 on each capillary column 32. While not shown a clear glass or plastic plate, for example, may be located over the substrate 30 to cover the columns and wells, as described above. Each of the wells 31, 33 and 34 and an end section of each of capillary columns 32 are provided with a coating, not shown, of electrically conductive material, as described above with respect to the FIGS. 1–2A and 2B embodiment. Also each set of the PCR wells 33 and the outer buffer wells 34 are interconnected by a passageway which is connected to the adjacent capillary column 32 to form a "T", for control of the PCR reaction material, as described above. In addition, the end sections of capillary columns 32 may be reduced in size, as in the FIGS. 1–2 embodiment.

Figure 4:
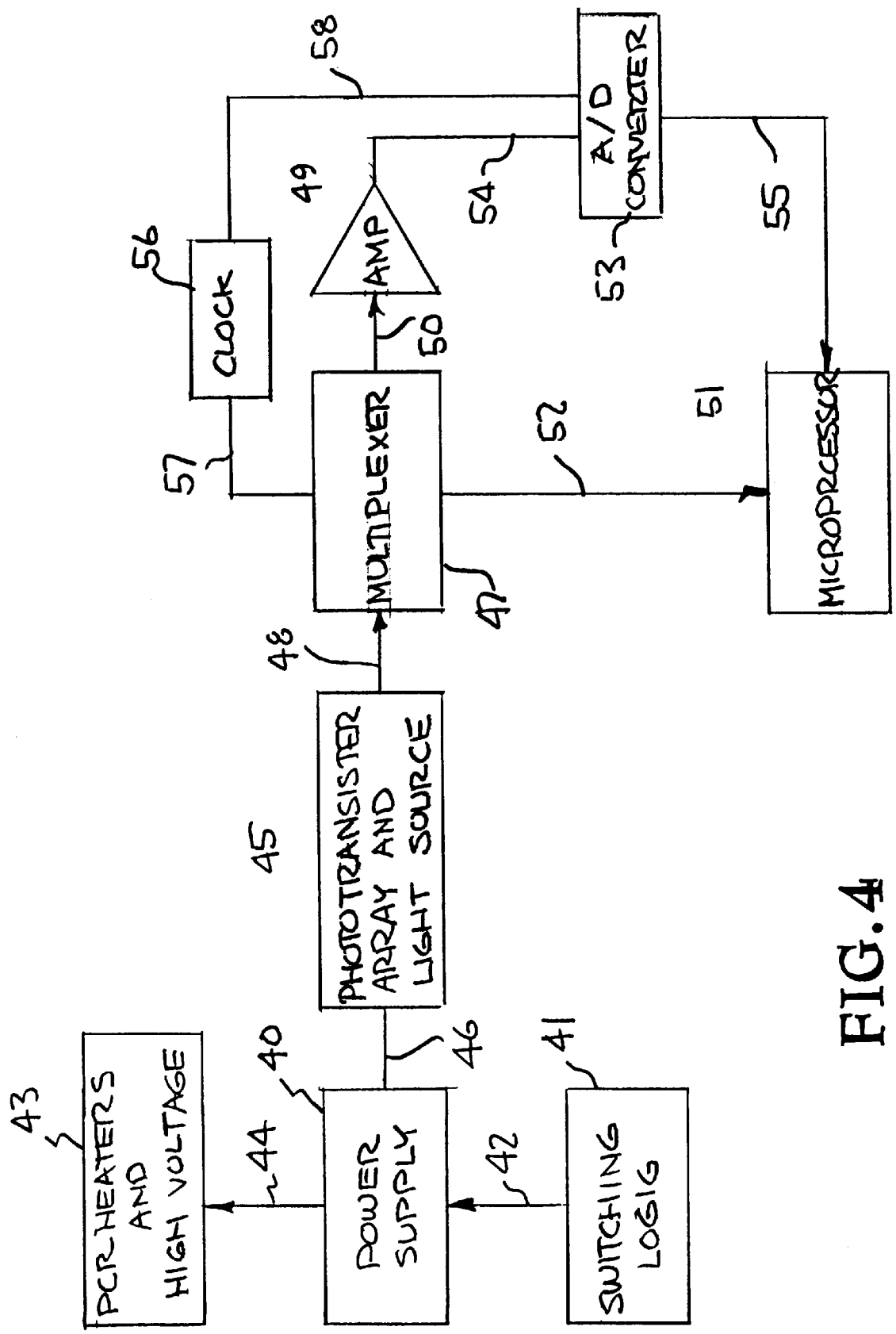
FIG. 4 illustrates a power supply and signal processing arrangement for multiple integrated PCR/CE channels such as the FIG. 3 embodiment.

FIG. 4 illustrates an embodiment of a power supply and output signal processing arrangement to the integrated PCR/CE instrument. As shown, the arrangement comprises a power supply 40 controlled by a switching logic 41 as indicated by arrow 42 and which provides high voltage for the electrophoresis columns, powers PCR heaters, and at 43 by arrow 44, and powers a photorensistor array and light source assembly 45, as indicated by arrow 46, the output of assembly 45 being fed into a multiplexer 47 as indicated by arrow 48, outputs from the multiplexer are directed to an amplifier 49 as indicated by arrow 50 and to a microprocessor 51 as indicated by arrow 52, the output of amplifier 49 is fed into an A/D converter 53 as indicated by line 54, with the output of A/D converter 53 being directed to microprocessor 51 as indicated by arrow 55, and a clock 56 is connected to mulitplexer 47 and A/D converter 53 as indicated by lines 57 and 58.

FIG. 5 schematically illustrates a prior art single capillary column optical detection system which could be modified for utilization in a multi-column CE system. In the illustrated detection system a sample photodiode 60 is located beneath a capillary column 61 in which is a capillary window 62, with a microfocusing lens 63 located between photodiode 60 and window 62, and microfocusing lenses 64 and 65 position adjacent an opposite or upper side of window 62. Positioned in alignment microfocusing lenses 64 and 65 is a fiberoptic beam splitter 66 to which is connected a reference photodiode 67 via lenses 68. A detector lamp 69 directs light indicated at 70 onto a diffraction grating 71 which diffracted light indicated at 72 is directed to fiber-optic beam splitter 66. Since the optical detection system of FIG. 5 is conventionally known and commercially available (Bio Focus 3000), description of the operation is deemed unnecessary.

It has thus been shown that the present invention provides an integrated PCR/CE instrument, particularly adopted for quick DNA-fragment analysis, but which can be utilized for numerous other organism detection/quantification applications. The combined PCR and Capillary Electrophoresis (CE) instrument provides the following: 1) PCR performed in a heat-cycled well attached directly to a micron-sized capillary electrophoretic channel; 2) PCR allowed to go to completion (e.g., 30 cycles) and then products drawn into channel with stain (buffer); 3) electrophoresis started ($T_O$ dock started); 4) photodiode picks off bands as they pass through the CE channel; 5) single and multiple PCR/CE lanes can be run; 6) generate up to 100 simultaneous PCR-CE lands or channels on a single substrate; and 7) a PCR-CE instrument that is disposable and can operate as a hand-held instrument.

While particular embodiments, materials, paraments, etc., have been set forth to exemplify and describe the principles of the invention, such are not intended to be limiting. Modifications and changes may become apparent to those skilled in the art, and it is intended that the invention be limited only by the scope of the appended claims.

The invention claimed is:

1. An integrated polymerase chain reaction/capillary electrophoresis instrument, comprising:
   a substrate;
   said substrate containing at least one capillary column formed therein;
   said at least one capillary column including end sections having a cross-section smaller than a main section thereof;
   said substrate including at least one well for polymerase chain reactions located adjacent one end of said capillary column;
   said substrate including at least one well for capillary electrophoresis buffer material located adjacent said one end of said capillary column;
   said substrate including a passageway interconnecting said wells and said one end of said capillary column located intermediate said wells;
   means for providing electrical power to said wells and said capillary column; and
   means for detecting material passing through said at least one capillary column.

2. The instrument of claim 1, additionally including means for covering the capillary column and the wells.

3. The instrument of claim 2, wherein said covering means comprises a glass plate.

4. The instrument of claim 1, wherein said means for providing electrical power includes a coating of electrically conductive material on surfaces forming said wells, the passageway, and end sections of said capillary column.

5. The instrument of claim 1, additionally including another well for containing buffer material located at an end of said capillary column opposite said one end connected to said wells for polymerase chain reactions and for capillary electrophoresis buffer material.

6. The instrument of claim 1, wherein said substrate includes a multiplicity of capillary columns, a well for polymerase chain reactions for each capillary column, and at least one well for capillary electrophoresis buffer material for each capillary column, said wells being connected to ends of said capillary columns.

7. The instrument of claim 6, wherein each of said substrate includes at least one well for buffer material located at an opposite end of said capillary columns.

8. The instrument of claim 6, wherein each capillary column terminates in a common buffer well.

9. The instrument of claim 1, wherein said substrate has a configuration selected from the group consisting of rectangular and circular.

10. The instrument of claim 1, wherein at least said wells and said passageway includes an electrically conductive coating, and wherein said means for providing electrical power includes means for activating and deactivating said conductive coating for controlling passage of material from said well for polymerase chain reactions into said capillary column.

11. The instrument of claim 10, wherein said electrically conductive coating is selected from the group consisting of Pt/Pd, Ag, and Sn.

12. The instrument of claim 1, wherein said detecting means includes at least one photodiode located adjacent said at least one capillary column, and means for directing light onto at least said capillary column.

13. The instrument of claim 1, wherein at least said well for polymerase chain reactions is provided with means for supplying said well with reaction solution material.

14. A system which detects and identifies organisms by polymerase chain reactions followed by capillary electrophoresis, comprising:
   an integrated polymerase chain reaction/capillary electrophoresis instrument which includes at least one well for polymerase chain reactions, at least one capillary column, at least one well for capillary electrophoresis buffer material, and means for detecting material passing through said at least one capillary column, wherein polymerase chain reactions from said at least one well for polymerase chain reactions are passed directly into one end of said capillary column along with buffer material from said at least one well for capillary electrophoresis buffer material for electrophoresis identification,
   said capillary column including end sections having a cross-section smaller than a main section thereof,
   said means for detecting material passing through said at least one capillary column being located in said main section of said at least one capillary column.

15. The system of claim 14, wherein said instrument comprises more than one capillary column, a polymerase chain reaction chamber located adjacent an end of each capillary column, and at least one chamber for containing buffer material located adjacent said end of each capillary column.

16. The system of claim 15, wherein opposite ends of said capillary columns terminate in a common chamber for containing buffer material.

17. The system of claim 15, wherein said capillary columns, said reaction chambers, and said chamber for containing buffer material are located on a single substrate.

18. The system of claim 17, additionally including a coating of electrically conductive material on the reaction chambers, the buffer material chambers, and at least one end of said capillary column.

* * * * *